United States Patent [19]

Sauder

[11] 4,170,998
[45] Oct. 16, 1979

[54] PORTABLE COOLING APPARATUS

[75] Inventor: James W. Sauder, San Ysidro, Calif.

[73] Assignee: Chattanooga Pharmacal Company, Chattanooga, Tenn.

[21] Appl. No.: 728,262

[22] Filed: Sep. 30, 1976

Related U.S. Application Data

[63] Continuation-in-part of Ser. No. 616,909, Sep. 26, 1975, Pat. No. 4,026,299.

[51] Int. Cl.² ............................................. A61F 7/00
[52] U.S. Cl. ................................... 128/400; 62/199; 62/259
[58] Field of Search .................... 128/68.1, 82.1, 379, 128/380, 399, 400, 402; 62/197, 149, 196 B, 198, 199, 524, 259 B

[56] References Cited

U.S. PATENT DOCUMENTS

| 1,422,886 | 7/1922 | Owens | 62/198 |
|---|---|---|---|
| 1,896,953 | 2/1933 | Hassell | 128/400 |
| 2,319,542 | 6/1940 | Hall | 128/400 |
| 2,504,308 | 4/1950 | Donkle | 128/400 |
| 2,691,870 | 10/1954 | Smith | 62/196 B |
| 2,696,084 | 12/1954 | Kirkpatrick | 62/198 |
| 2,746,259 | 5/1956 | Katzenberger | 62/198 |
| 2,951,350 | 9/1960 | Etherington et al. | 62/149 |
| 3,071,935 | 1/1963 | Kapeker | 62/196 B |
| 3,074,410 | 1/1963 | Foster | 128/400 |
| 3,201,950 | 8/1965 | Shrader | 62/197 |
| 3,220,414 | 11/1965 | Johnston | 128/400 |
| 3,238,944 | 3/1966 | Hirschhorn | 128/400 |
| 3,257,819 | 6/1966 | Maloney | 62/199 |
| 3,364,693 | 1/1968 | Jacobs | 62/196 B |
| 3,477,240 | 11/1969 | Thoren et al. | 62/197 |
| 3,504,674 | 4/1970 | Swenson et al. | 128/400 |
| 3,507,321 | 4/1970 | Palma | 128/400 |
| 3,736,763 | 6/1973 | Garland | 62/149 |
| 3,743,010 | 7/1973 | Farney et al. | 62/196 B |
| 3,785,375 | 1/1974 | Lipson | 128/82.1 |
| 3,871,381 | 3/1975 | Roslonski | 128/400 |
| 3,889,684 | 6/1975 | Lebold | 128/402 |
| 3,916,911 | 11/1975 | Sauder et al. | 128/400 |
| 3,967,627 | 7/1976 | Brown | 128/400 |

Primary Examiner—Robert W. Michell
Assistant Examiner—Arthur S. Rose
Attorney, Agent, or Firm—Bell, Seltzer, Park & Gibson

[57] ABSTRACT

An improved portable refrigeration apparatus for cooling a limb of a patient or the like, and which includes at least one flexible pad adapted to be wrapped around a bodily limb and which incorporates flexible tubing serving as an evaporator. A separate auxiliary evaporator is positioned downstream of the pad to insure that all of the refrigerant is evaporated before returning to the compressor. Also, there is provided a temperature control system for the pad which includes a by-pass conduit which by-passes the pad, and a temperature controlled valve for selectively opening and closing the by-pass conduit, and so that the refrigerant will flow concurrently through the by-pass conduit and the pad when the valve is opened. In one embodiment, a positive pressure device is provided for maintaining a selected refrigerant pressure in the pad and to thereby prevent a possible vacuum in the tubing of the pad, and in addition, there may be provided a resistive heating element at the pad so that the apparatus may be selectively used for heating the limb of a patient.

15 Claims, 6 Drawing Figures 4,170,998

PORTABLE COOLING APPARATUS

BACKGROUND OF THE INVENTION

This application is a continuation-in-part of my co-pending application Ser. No. 616,909 filed Sept. 26, 1975, and now U.S. Pat. No. 4,026,299.

In U.S. Pat. No. 3,916,911, there is disclosed a portable heating and cooling apparatus utilizing flexible pads to be wrapped around the limb or other body portion of a human or animal, for selectively heating or cooling that body portion. The portable apparatus is especially useful in treating sprains, strains or other muscular injuries to athletes or race horses, as soon after the injury occurs as possible in order to rapidly reduce swelling, fever or the like to the injured area. Such a device obviates the inconvenient use of ice packs for treating such injuries or muscular diseases or inflammation.

In my co-pending application, there is further disclosed an improvement of the patented device for both heating and cooling, selection being made by a reversing valve and utilizing at least one flexible pad and tubing as well as quick-connect couplings between the apparatus and the cooling and heating pads. The apparatus of the present invention, unlike the heat pump design of my previous application, utilizes a refrigerant directing apparatus and cooling tubing and pad, but is designed with an auxiliary evaporator cooperating with a by-pass conduit and valve, preferably thermostatically operated, so that the cooling pad temperature may be selected and maintained automatically. In addition, a preferred embodiment includes the use of a resistance heating element secured in the pad adjacent the cooling tubing so that when desired, the apparatus may be used to heat with the refrigerant directing components inactive. Other features, embodiments and advantages of the apparatus of the invention will be more fully explained hereinafter.

SUMMARY OF THE INVENTION

The apparatus of the present invention comprises a cooling device utilizing refrigerant composition and conduits for directing it through the components including a compressor, condenser and fan, and cooling pad and tubing, acting as an evaporator and for being wrapped around a warm body portion such as an arm, leg or any other desired portion of the body to be cooled. The device also includes an auxiliary evaporator disposed along the refrigerant directing conduit system between the cooling pad and the compressor. A by-pass pipe intersects the conduit upstream from cooling pad for selectively directing refrigerant to the auxiliary evaporator thereby by-passing the pad and tubing. The by-pass pipe is open and closed by a valve, preferably thermostatically operated, and sensing temperature at the cooling pad and which thermostat may be regulated by suitable temperature selecting control means. Another important feature that may be incorporated is a positive pressure device comprising a supply line extending from the high side of the compressor and to the auxiliary evaporator thereby by-passing the condenser and an expansion valve in the line for maintaining a selected refrigerant pressure in the system. Additional embodiments, advantages and uses of the apparatus will be evident from the following detailed description.

DETAILED DESCRIPTION OF THE INVENTION

Figure 1:
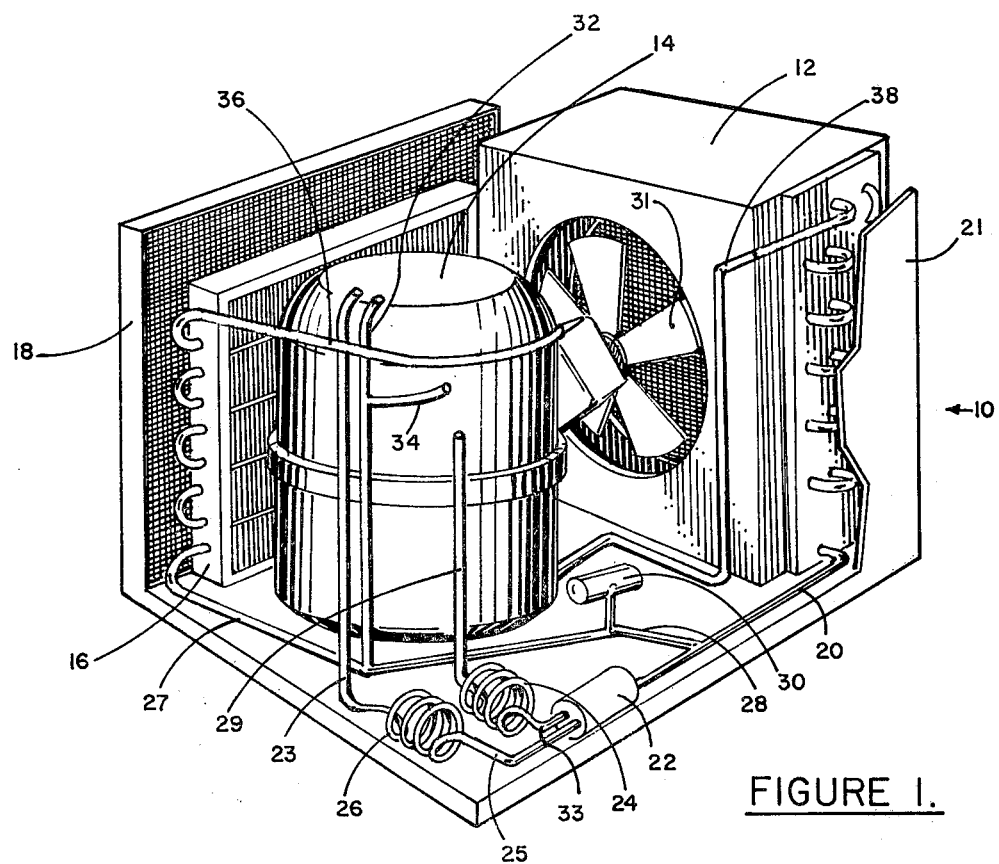
FIG. 1 is an illustration of the internal components of one embodiment of the apparatus of the invention, showing the by-pass pipe feature.

Observing first FIG. 1 of the drawings, there is illustrated the apparatus generally 10 which is enclosed in a case member 21, shown cut away in order to expose the apparatus components. Major components include a condenser 12 and cooperating fan 31 for directing air past the condenser coils to condense refrigerant composition therein. Compressor 14 compresses gaseous refrigerant composition directed from conduit 36 and auxiliary evaporator 16. The latter includes a length of thermally conductive tubing, usually copper coils, for further increasing the temperature of the refrigerant as it is returned from the cooling pad and the tubing. Conduit 38 directs refrigerant composition from the compressor 14 to the condenser 12.

Conduits 32 and 34 direct refrigerant composition returning from the cooling pad and tubing to the auxiliary evaporator 16 via conduit 27. From condenser 12, conduit 20 directs refrigerant composition through dryer 22, into the two conduit segments 25 and 33, through capillary tubes 26 and 24 respectively, and to cooling pads and tubing via conduits 23 and 29. Thus, the apparatus shown illustrates that used for a device having two cooling pads, it being understood where only one cooling pad is used, only one capillary tube and outlet and inlet conduits are required.

Figure 2:
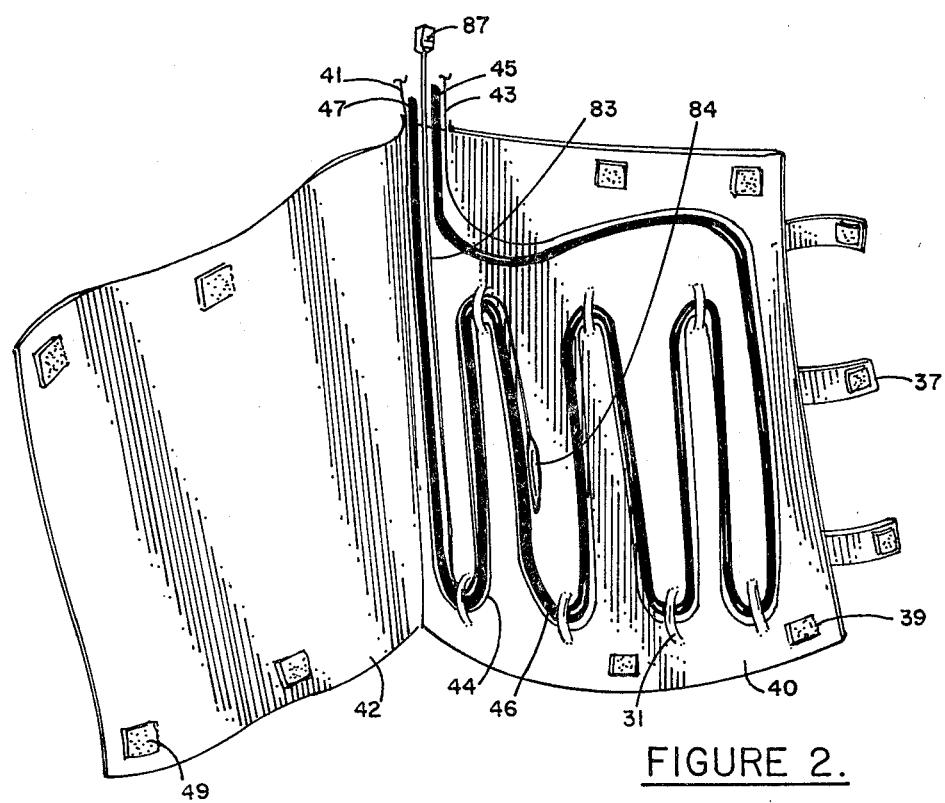
FIG. 2 is a view of an open flexible pad, cooling tubing and resistive heating element.

FIG. 2 illustrates the flexible pad utilized to be wrapped around a warm body portion to be cooled. The open pad shown has an outside flexible insulating sheet 40, preferably composed of a rubber composition and having a fabric back layer, such material commonly being used for wet suits and the like. Such a rubbery composition provides excellent heat insulation and at the same time is reasonably lightweight and easy to form to any desired shape around a limb or other body portion. Secured to the inside of the insulating sheet 40 is a flexible hose or tubing 46 for directing refrigerant composition to and from the pad and which tubing may be removably secured by a plurality of straps 31. These straps may be secured to the inside insulating pad surface using snaps, buckles or the like, or preferably Velcro, a material in which one mating surface has a plurality of fabric loops while the opposite surface comprises small, flexible barbs or hooks for engaging the loops. Such material is described in further detail, for example, in U.S. Pat. Nos. 3,461,511 or 3,387,345. Regardless of the type of disengagable device used for securing the ends of straps 31, a plurality of such straps are located at selected positions on the interior surface of the insulated sheet 40 by which the flexible refrigerant directing conduit or tubing is secured to the sheet. The removable straps allow for removing the tubing from the pad where pad replacement is desired. Moreover, because the cooling tubing is flexible, different shaped cooling pads may be desired for use on different limbs or body portions. Thus, the cooling tubing simply can be removed from one cooling pad and placed in another pad as desired.

Non-thermal insulating sheet 42 is also removably secured by utilizing Velcro fasteners 49 and 39 or other means such as snaps, zippers and the like. Should non-insulating sheet 42 become soiled or worn it may be removed and washed or otherwise cleaned for sanitary purposes, or replaced. It will also be understood that this non-insulating sheet lies against the patient's skin so that the cold from the cooling tubing is readily directed to the patient's limb or warm body portion. Moreover, removal or disengagement of the non-insulating sheet exposes the tubing for repairs or replacement. Additional features of the pad includes straps 37 also having snaps or Velcro closure means cooperating on the pad so that the pad simply may be wrapped around the patient and secured. Other features of such a pad are disclosed fully in my aforesaid parent application, the description thereof being further incorporated herein by reference.

Although only one flexible pad and cooling tubing are shown, it will again be understood that a plurality of such pads may be used, depending on the size of the apparatus, including the compressor and condenser. In utilizing the single pad shown, tubing end 47 would be connected to conduit 34 whereas tubing end 45 will be connected to conduit 29 of the apparatus shown in FIG. 1. Thus, cold refrigerant composition will pass from outlet conduit 29 through the tubing in the cooling pad and return at the opposite tubing end via conduit 34 where it will be directed via conduit 27 into the auxiliary evaporator 16. It is convenient to incorporate quick-connect couplings to allow for easy connection or disconnection between the pad or pads and apparatus. Such couplings are of the type referred to, for example, in U.S. Pat. No. 2,823,048 and which couplings are conveniently incorporated on a top panel for the apparatus (not shown) and as further described in my parent application.

Figure 6:
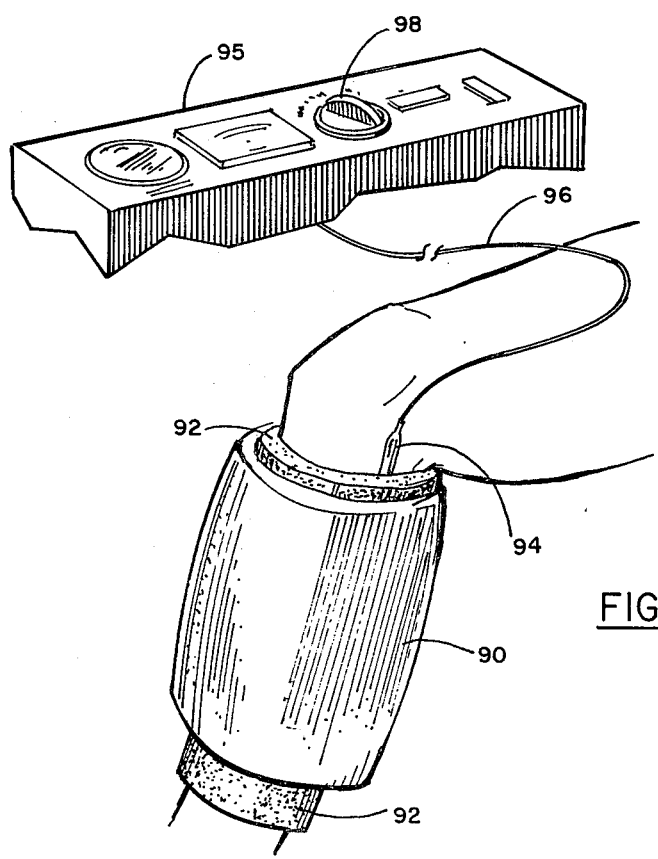
FIG. 6 shows a skin temperature probe for thermostatically controlling the cooling apparatus.

As previously noted, a significant improvement of the apparatus of the present invention is the incorporation of a by-pass pipe and cooperating valve for maintaining selected pad cooling temperatures. Such a pipe 28 is shown in FIG. 1 interconnecting conduits 20 and 27. Solenoid valve 30 opens and closes pipe 28. When the valve opens the pipe, refrigerant composition will pass through the pipe into conduit 27 and auxiliary evaporator 16 thereby by-passing dryer 22, capillary tubes 24 and 26 and the cooling tubing and pads. Instead, the cooled refrigerant composition is directed to the auxiliary evaporator and circulates through the apparatus without further cooling the pad and flexible tubing. Actually, as refrigerant flows into conduit 27, this causes a back pressure to build up in the pads and tubing which concomitantly elevates the pad temperature. Preferably, the valve cooperating with by-pass pipe 28 and which opens and closes the by-pass pipe, is responsive to a thermostat control. A thermostat will monitor temperature at the cooling pad and when the pad temperature is elevated past a selected temperature the valve closes the by-pass pipe thereby directing the cooled refrigerant composition through the tubing at the cooling pad. When the pad has again cooled to the selected temperature, the sensing thermostat will cause the by-pass valve to open, whereupon refrigerant composition by-passes the pad. Preferably, the thermostat control will include a temperature selecting member such as a selector control and thermometer scale located on the apparatus control panel, as shown in FIG. 6 and illustrated in my aforesaid parent application. Accordingly, the desired pad temperature can simply be dialed or otherwise selected and the apparatus, when functioning, will maintain selected temperature at the cooling pad, again, by periodically opening and closing the by-pass pipe.

Figure 3:
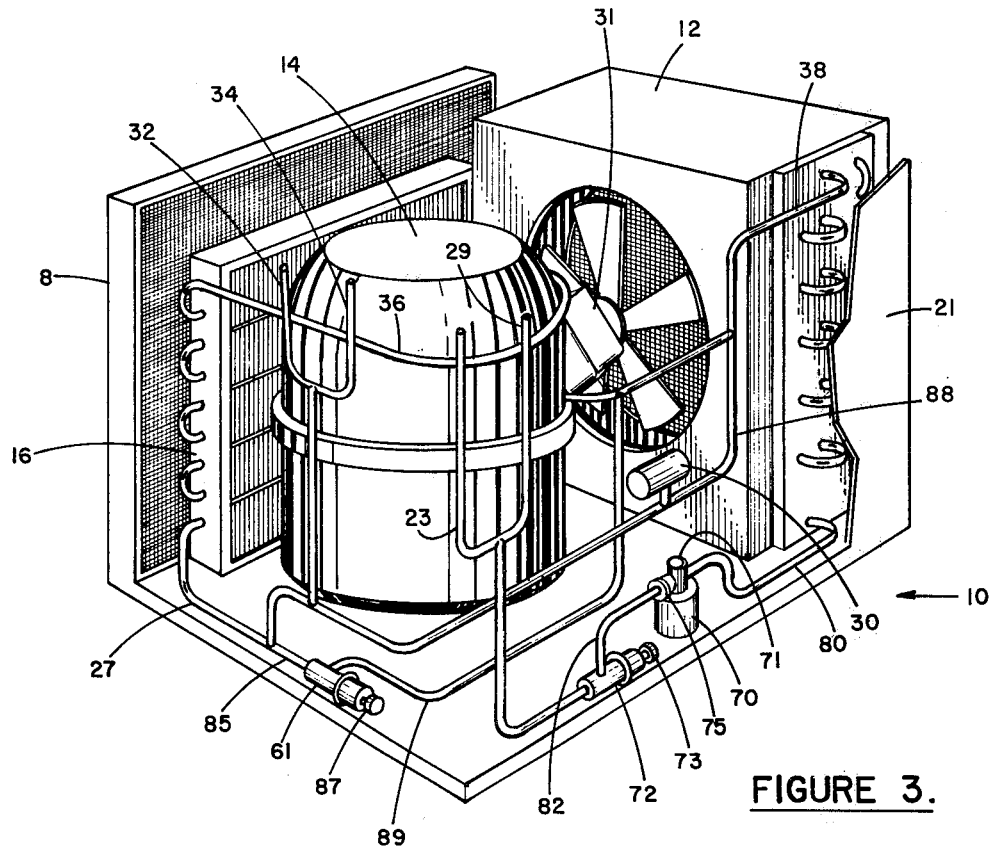
FIG. 3 is an illustration of internal components of another embodiment of the invention.

FIG. 3 illustrates an alternative embodiment for the by-pass pipe and valve when utilizing an expansion valve instead of the capillary tubes shown in FIG. 1. For some applications it may be preferred to use an expansion valve since such a valve incorporates means for manually adjusting minimum pad temperatures. Moreover, the use of an expansion valve also allows the incorporation of a receiver or reservoir for storing additional refrigerant composition for automatically compensating for any refrigerant losses during operation of the apparatus. The use of such a receiver or reservoir thus eliminates the necessity for charging refrigerant composition to the apparatus in case of minor leakage which may occur throughout the conduit and tubing system, especially where rubber tubing is used in the flexible cooling pads. It will be understood that such rubber tubing normally has some inherent porosity, thus causing some loss of refrigerant during normal usage.

Referring specifically to FIG. 3, conduit portion 80 receives refrigerant composition from condenser 12 where it passes through dryer 75, conduit 82 and into expansion valve 72. From the expansion valve, the refrigerant then passes to the cooling pads (not shown) via conduits 23 and 29. Expansion valve 72 incorporates a manual knob 73 so that an operator may select or vary the extent of composition expansion in the valve and concomitantly the temperature characteristics of the cooling pad. Between conduits 80 and 82 also is located receiver or refrigerant reservoir 70 which holds a supply of refrigerant, for example, about 16 ounces. A sight glass 71 may also be present for observing refrigerant flow and any bubbles or other indications of low refrigerant composition in the system as it passes the glass.

In the embodiment shown in FIG. 3, the by-pass pipe 88 intersects conduit 38 between compressor 14 and condenser 12 rather than in the mode illustrated in FIG. 1. The reason for by-passing the condenser in the embodiment illustrated in FIG. 3 is due to the fact that when utilizing an expansion valve and receiver or reservoir in the apparatus, there may be more liquid refrigerant delivered to the auxiliary evaporator in the by-pass mode than it can handle. This is not a problem when utilizing the capillary tubes and without a refrigerant composition reservoir shown in FIG. 1. However, because it is a potential problem when utilizing the arrangement of FIG. 3, it is preferred to divert the refrigerant composition during by-pass to the auxiliary evaporator from the high side of the compressor prior to condensation in the condenser. Otherwise, the apparatus illustrated in FIG. 3 operates much like that shown in FIG. 1. When the cooling pad has been cooled to the desired temperature, the thermostat sensor will actuate solenoid valve 30 which will open conduit 88 thereby sending the refrigerant composition to conduit 27 and into auxiliary evaporator 16 and by-passing condenser 12, expansion valve 72, and the cooling pads.

In still another embodiment, a positive pressure device may be incorporated to maintain a minimum pressure in the pad or pads and tubing. Thus, this feature is desirable in order to avoid possible vacuum in the cooling pad tubing. Since this flexible tubing may consist of rubber or synthetic elastomer, which may be slightly porous, if a vacuum were to occur because of low refrigerant composition in the system, air would be taken into the tubing and passed through the system which could cause contamination as well as damage to the compressor. In order to avoid such a situation, a positive pressure device consisting of a conduit and a manually regulated expansion valve are used. Such a feature is illustrated further in FIG. 3, although it must be appreciated that it can also be used with the apparatus shown in FIG. 1 as well (see FIG. 4). A positive pressure device consists of a supply line or conduit 89 which taps or communicates with conduit 38 on the compressor high side. The supply line extends to expansion valve 61 and supply line 85 communicates with conduit 27 which then enters auxiliary evaporator 16. Expansion valve 61 may be adjusted by an operator utilizing manual adjustment knob 87 so that when the pressure in the system falls to or below a selected minimum pressure to which expansion valve 61 has been set, for example, 1-2 psi., it will cause the valve to open thereby directing the refrigerant composition from conduit 38 into line 89, expansion valve 61, line 85, conduit 27 and into the auxiliary evaporator. This flow of refrigerant composition will continue until such time as the pressure in the system has again exceeded the minimum pressure. Thus, by so directing the composition, it will cause a back pressure to be created in the pad tubing and will prevent the creation of possible vacuum in the cooling pad tubing. It will also be noted in FIG. 3, that supply line 89 intersects or communicates with conduit 38 upstream from by-pass pipe 88. Again, this positive pressure system may be used even without a by-pass system so long as an auxiliary evaporator is present. The auxiliary evaporator functions to impart additional heat to the refrigerant, and insures that no liquid refrigerant is passed on to foul the compressor.

Referring again to FIG. 2, the use of a resistive heating wire or coil is illustrated. The purpose for such an embodiment is to provide the apparatus of the invention with a heating capability separate and distinct from the refrigerant cooling operation previously described. Thus, there is incorporated a heating wire 44 conveniently placed along side or otherwise adjacent the cooling coil within the pad utilizing the same tie down or securing straps 31. The ends 41 and 43 of the heating element are shown and these will be secured properly to a switching member whereby a current will be supplied simply by flipping an on-off switch on the apparatus control panel. Normally, such a heating function will not be used when the pad is to be used for cooling a warm body portion. Instead, with the compressor and other refrigerant cooling components are not operating, the pad simply may be used for providing heat to a patient where injury dictates that heat be applied instead of cooling. It will be understood that the resistive heating wire will be insulated and of the type that can be safely incorporated adjacent the flexible cooling tubing and secured in a flexible pad of the type shown in FIG. 2 and previously described.

Figure 4:
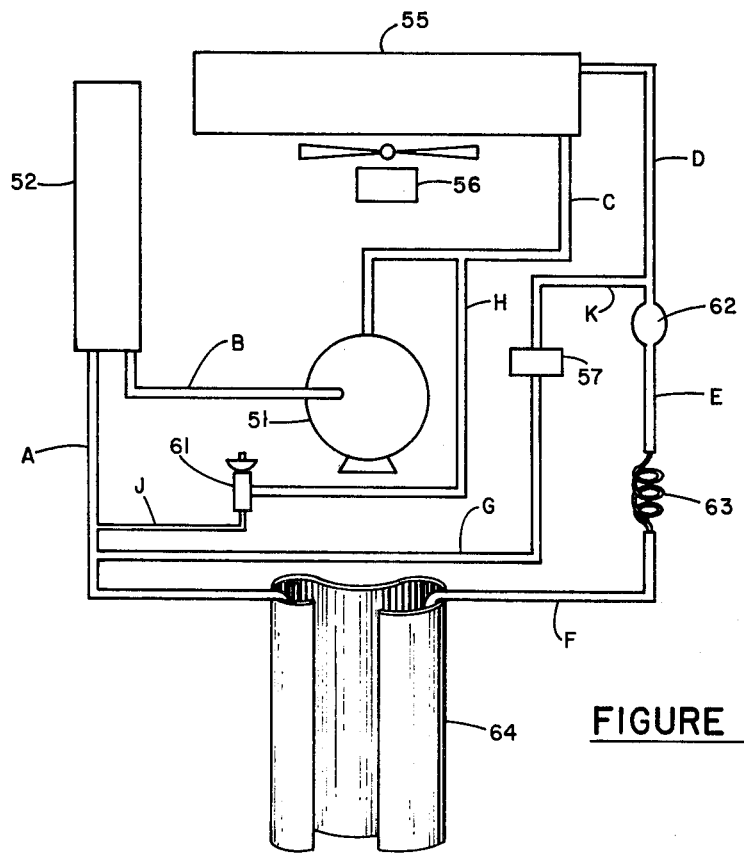
FIGS. 4 and 5 are schematic views illustrating alternative apparatus component embodiments in directing refrigerant flow.
Figure 5:
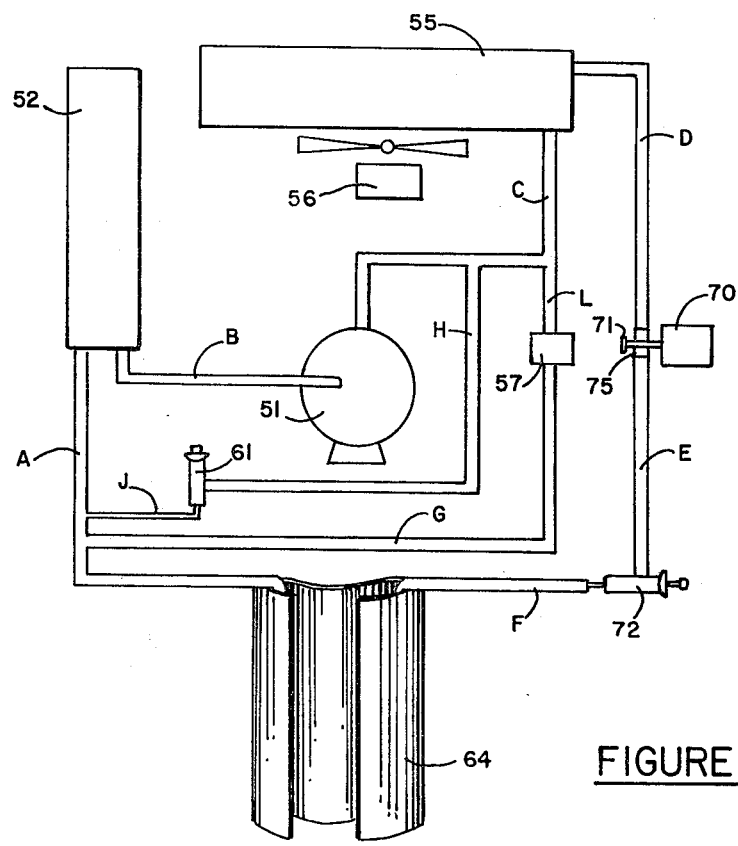

Observing now FIGS. 4 and 5, there is shown schematically the apparatus of the invention including the conduits for directing refrigerant composition and the cooling pad 64 having the flexible tubing therein and which pad and tubing are wrapped around a warm body portion to be cooled. It will be appreciated that the pad and tubing act as an evaporator for the refrigerant composition. FIG. 4 illustrates the apparatus shown in FIG. 1 with the addition of a positive pressure device embodiment while FIG. 5 is directed to the apparatus of FIG. 3. Referring first to FIG. 4, in operation, refrigerant composition is directed via conduit A to auxiliary evaporator 52 where it absorbs further energy by being heated. The refrigerant compositions leaves auxiliary evaporator 52 via conduit B and enters compressor 51. Thereafter, the composition is forced via conduit C into condenser 55 where it is cooled as it passes through the condenser coils and which cooling is aided by fan 56 which directs relatively cool ambient air over fins normally associated with the condenser coils. From the condenser, the refrigerant composition is directed along conduit D. Where pad 64 is to be cooled, the refrigerant is directed through dryer 62 where desiccant removes any moisture. Normally, the dryer will also preferably include a filter or strainer, for example, a 100 mesh screen, so as to prevent any particulate matter from entering capillary tube 63 via conduit E. Thereafter, the cooled refrigerant composition is directed to the pad via conduit F. When the pad has attained a suitably low temperature selected by an operator, a thermostat sensing the pad temperature electrically energizes solenoid valve 57 which valve opens conduit G and the refrigerant composition bypasses the dryer, capillary tube and cooling pad and is directed to conduit A and again to the auxiliary evaporator. This refrigerant flow path is maintained until cooling pad 64 has become warm enough to require further cooling which condition is again sensed by a thermostatic sensor which energizes solenoid valve 57 and then closes by-pass pipe G.

In addition to the above discussed components regarding FIG. 4, the positive pressure device is a line or conduit H which communicates with conduit C downstream from condenser 55 but upstream from compressor 51 and an expansion valve 61, which may be adjusted to maintain any desirable minimum pressure in the system as previously described. Supply line J then directs refrigerant composition from the expansion valve to conduit A and auxiliary evaporator 52.

FIG. 5 shows schematically the apparatus of FIG. 3 whereby refrigerant composition travels in the manner described regarding FIG. 4 with the major difference being that this embodiment incorporates a receiver or reservoir for refrigerant composition and expansion valve 72 in place of capillary tubes. The receiver includes a dryer 75 and may also incorporate a window 71 for observing refrigerant flow in the conduit. When pad 64 is to be cooled, refrigerant composition travels from compressor 51 via conduit C through condenser 55, through conduits D and E and into expansion valve 72, through conduit F and cooling pad 64, conduit A into auxiliary evaporator 52 and back to compressor 51 via conduit B. Once the cooling pad has achieved the desired low temperature, upon command from a sensing thermostat, valve 57 will open whereby refrigerant composition will pass from compressor 51 through conduits L, G, A, auxiliary evaporator 52 and back to compressor via conduit B. This condition will continue until further cooling of cooling pad 64 is required whereupon valve 57 will close and the composition will then be directed as previously described. Again, the incorporation of a positive pressure device comprising conduits H and J with manually adjustable expansion valve 61 may be used. It should be appreciated that the positive pressure device may be used with or without the by-pass lines described so long as an auxiliary evaporator is present in the apparatus.

As previously mentioned, it is desirable to thermostatically operate the cooling apparatus by sensing the pad temperature. FIG. 2 illustrates a temperature sensing probe 84 secured to the pad insulated sheet 40 adjacent the cooling tubes so that the pad temperature is monitored and the by-pass pipe in the apparatus is automatically opened and closed in response to the monitored temperature. Probe 84 is secured at the end of insulated conductive wire 83 and disconnecting plug 87 which may be attached to a plug and wire leading to the apparatus control panel. Thus, the temperature probe may be moved with the pad or independently replaced or repaired.

FIG. 6 shows the use of such a probe 94 and wire 96 for sensing the skin temperature rather than pad temperature. This feature is especially desirable when treating a patient wearing a cast 92 as is illustrated. For example, it may be desirable to reduce swelling of a limb on which a cast is located. Yet, since a cast, usually plaster, is itself thermally insulating, temperature selection and maintanence will be different than when the pad is directly applied to a limb. It may be necessary to maintain pad temperature at 20°-40° F. in order to achieve and hold skin temperature of 60° F., and this will vary with the cast thickness and composition. Accordingly, it is highly desirable and advantageous to insert a temperature sensing probe 94 between cast 92 and the patient's skin. Cooling pad 90 will supply cooling to the cast in response to the temperature sensing probe, which will open and close electronic switching means for actuating the by-pass pipe valve feature of the apparatus in the manner previously explained. Conveniently a temperature scale on control panel 95 will be indexed for a desirable temperate range and a temperature selection control 98 will then be set to the specific temperature to be monitored by the probe and maintained by the by-pass valve feature. Such skin temperature selection is also very desirable for patients who are quite sensitive to cold and have low cold exposure tolerance. Thus, the cold temperature selection and maintenance feature of the invention is a highly advantageous embodiment, made possible by the by-pass valve and pipe and auxiliary evaporator components.

The type of temperature probes used for skin or pad temperature monitoring is not critical. State of the art devices include temperature sensitive materials and cooperating resistors, etc., usually sealed in a hard resin cover. Conveniently the skin probe cover may have a flat side or sides for lying against the patient's skin and of a thickness suitable for sliding between the skin and a cast.

Again, it will be further understood by those skilled in the art that the pad by-pass features disclosed herein do not actually result in completely by-passing or isolating the cooling pads and tubing. Instead, when the by-pass pipe or the positive pressure expansion valve are opened, the flow of refrigerant composition therein causes a back pressure in the pad or pads as some refrigerant will continue to be provided to the pads and because of significant refrigerant flow into the conduit between the pads and auxiliary evaporator. In either case, this will cause increased pressure in the pads and concomitant temperature increase.

The apparatus of the invention is preferably enclosed in a case, such as a portable carrying case as disclosed in my aforesaid parent application. Again, different sized and shaped cooling pads may be used as means for injecting make-up refrigerant composition in the disclosed apparatus as described in my parent application and which description is incorporated herein by reference. Although the cooling pad has been described as used with flexible tubing, normally of a rubber or synthetic elastomer type, it is also within the scope of the invention to use any tubing which may be secured to the cooling pad to be wrapped around a warm body portion to be cooled. For example, a ductile copper tubing as disclosed in the aforesaid patent may be used. These as well as other embodiments within the purview of the invention will be evident to those skilled in the art.

I claim:

1. A portable apparatus for cooling a limb of a patient or the like and comprising a compressor, a condenser, expansion valve means, at least one flexible pad adapted to be wrapped around a bodily limb and including flexible tubing serving as an evaporator, an auxiliary evaporator, conduit means for circulating a refrigerant composition serially from said compressor to said condenser, to said expansion valve means, to said tubing, to said auxiliary evaporator and back to said compressor, a by-pass conduit operatively connected to said conduit means and extending from a point downstream of said compressor and upstream of said pad to a point downstream of said pad and upstream of said auxiliary evaporator, and by-pass valve means for selectively opening and closing said by-pass conduit and so that the refrigerant composition will flow concurrently through the by-pass conduit and through the flexible tubing of said pad when said by-pass conduit is open, whereby the temperature of said pad may be controlled by the opening and closing of said by-pass valve means.

2. The apparatus as defined in claim 1 wherein said by-pass valve means includes means for monitoring the temperature at said pad, and means for closing said by-pass valve means when the temperature at the pad is above a pre-selected temperature, and for opening said by-pass valve means when the temperature at the pad is below a pre-selected temperature.

3. The apparatus as defined in claim 2 wherein said temperature monitoring means comprises a temperature sensing probe secured to said pad.

4. The apparatus as defined in claim 1 wherein said expansion valve means comprises a capillary tube, and wherein said by-pass conduit extends from a point downstream of said condenser and upstream from said capillary tube to said auxiliary evaporator.

5. The apparatus as defined in claim 1 wherein said expansion valve means comprises an expansion valve, and wherein said by-pass conduit extends from a point downstream from said compressor and upstream from said condenser to said auxiliary evaporator.

6. The apparatus as defined in claim 5 further comprising a refrigerant composition reservoir communicating with said conduit means upstream from said expansion valve for maintaining a supply of said composition in said apparatus.

7. The apparatus as defined in claim 1 further comprising positive pressure means for maintaining a selected refrigerant composition minimum pressure in said tubing, said positive pressure means comprising a supply line communicating with said conduit means downstream from said compressor and extending to said auxiliary evaporator, and valve means in said supply line.

8. The apparatus as defined in claim 1 wherein said pad further includes a resistive heating element to permit the heating thereof.

9. The apparatus as defined in claim 1 further comprising a fan operatively associated with said condenser for facilitating the removal of heat therefrom.

10. The apparatus as defined in claim 1 wherein said pad further comprises a flexible thermal insulating outer sheet, a flexible inner sheet, and means for releasably interconnecting said outer and inner sheets in an overlying relationship and with said flexible tubing disposed therebetween.

11. The apparatus as defined in claim 10 wherein said pad further comprises means for releasably holding the same in a wrapped position around the bodily limb.

12. The apparatus as defined in claim 11 wherein said flexible tubing is disposed in a serpentine configuration and is releasably secured to said outer sheet.

13. The apparatus as defined in claim 1 wherein said auxiliary evaporator is positioned with respect to that portion of said conduit means between said compressor and pad so as to be substantially free of any heat exchange relationship therewith.

14. The apparatus as defined in claim 13 wherein said auxiliary evaporator is positioned immediately adjacent said compressor.

15. The apparatus as defined in claim 13 wherein said by-pass conduit extends from a point downstream from said compressor and upstream from said condenser to said auxiliary evaporator, and wherein said apparatus further comprises positive pressure means for maintaining a selected refrigerant composition minimum pressure in said tubing of said pad, said positive pressure means comprising a conduit line communicating with said conduit means at a point downstream from said compressor and upstream from said condenser and extending to a point immediately upstream of said auxiliary evaporator, and pressure responsive valve means in said conduit line.

* * * * *